(12) United States Patent
Sibbitt

(10) Patent No.: US 6,183,449 B1
(45) Date of Patent: Feb. 6, 2001

(54) SAFETY CAPS FOR SHARPS

(76) Inventor: Wilmer L. Sibbitt, 338 Amherst, NE., Albuquerque, NM (US) 87106

(*) Notice: Under 35 U.S.C. 154(b), the term of this patent shall be extended for 0 days.

(21) Appl. No.: 09/262,118

(22) Filed: Mar. 4, 1999

(51) Int. Cl.[7] .................................................. A61M 5/32
(52) U.S. Cl. ........................................... 604/263; 604/192
(58) Field of Search ..................................... 604/192, 198, 604/263, 264, 110

(56) References Cited

U.S. PATENT DOCUMENTS

| | | |
|---|---|---|
| 4,643,722 | 2/1987 | Smith, Jr. . |
| 4,659,330 | 4/1987 | Nelson et al. . |
| 4,740,204 | 4/1988 | Masters et al. . |
| 4,840,272 | 6/1989 | Goldman . |
| 4,906,235 | 3/1990 | Roberts . |
| 4,985,020 | 1/1991 | Kasuya . |
| 4,994,046 | 2/1991 | Wesson et al. . |
| 5,067,944 | 11/1991 | Nichols . |
| 5,087,249 | 2/1992 | Deal . |
| 5,195,982 * | 3/1993 | Hoenig ................................... 604/192 |
| 5,207,653 | 5/1993 | Janjua et al. . |
| 5,389,083 | 2/1995 | McCarthy . |
| 5,411,492 * | 5/1995 | Sturman et al. ....................... 604/263 |
| 5,514,099 * | 5/1996 | McCarthy ............................. 604/192 |
| 5,630,803 | 5/1997 | Tamaro . |
| 5,643,219 | 7/1997 | Burns . |
| 5,688,253 | 11/1997 | Paradis . |
| 5,702,369 * | 12/1997 | Mercereau ............................ 604/192 |
| 5,807,351 | 9/1998 | Kashmer . |

OTHER PUBLICATIONS

Sibbitt, Wilmer L., Jr., MD, Needle Stick Prevention, from the Center for Non–Invasive Diagnosis and The Department of Internal Medicine, University of New Mexico School of Medicine, Albuquerque, NM 87131.

Sepkowitz, K.A., Occupationally Acquired Infections in Health Care Workers, Part II, *Ann. Intern. Med.* 1996; 125; 917–928.

Patterson et al., Occupational Hazards to Hospital Personnel, *Annals of Internal Medicine.* 1985; 102: 658–680.

Marcus, R., Surveillance of Health Care Workers Exposed to Blood from Patients Infected with the Human Immunodeficiency Virus, *The New England Journal of Medicine,* 1988, 319: 1118–1123.

Gerberding, Julie Louise, Management of Occupational Exposures to Blood–Borne Virus, *New England Journal of Medicine,* 1995; 332: 444–451.

Goldwater, P. N., Impact of a recapping device on venepuncture–related needlestick injury, *Infect Control Hospital Epidemiol* 1980: 10: 21–25.

Puro et al., Hepatitis C Virus Infection in Health Care Workers (Letter), *Infec. Control Hosp. Epidemiol* 1995; 16: 324–325.

Kiyosawa et al., Hepatitis C in Hospital Employees with Needlestick Injuries, *Annals of Internal Medicine.* 1991; 115: 367–369.

\* cited by examiner

Primary Examiner—John D. Yasko
(74) Attorney, Agent, or Firm—Jagtiani & Associates

(57) ABSTRACT

The present invention provides a safety cap for sharps which includes a handle which extends away from the sheath holding and covering the sharp.

13 Claims, 7 Drawing Sheets

SAFETY CAPS FOR SHARPS

BACKGROUND OF THE INVENTION

1. Field of the Invention

The present invention relates to safety devices for sharps such as the needles and blades of medical devices.

2. Description of the Prior Art

Accidental penetration of the skin from sharp instruments is one of the most common modes of transmission of fatal or debilitating infectious diseases to health care workers. Hepatitis B, hepatitis C, and HIV (the AIDS virus) in the health care environment are typically transmitted from needle sticks and result in years of debilitating illness, loss of productivity, workman's compensation payments, medical expenses, and accelerated mortality. Groups of health care workers most susceptible to needle sticks include nurses and laboratory workers, but physicians, dentists, dialysis workers, oral surgeons, medical waste workers, and animal handlers are also exposed. Using a standard cap, recapping a hypodermic needle is an extremely dangerous procedure, entailing a significant risk of needle stick per capping attempt. OSHA requires regular instruction of health care workers in techniques to prevent accidental needle sticks, yet needle sticks, especially those from recapping, remain an important mechanism for transmission of virulent infectious agents to health care workers. Any advances in medical instrument design that would limit or prevent needle sticks would markedly reduce the health risks from infectious diseases for health care workers and would result in considerable savings from lost productivity, medical costs, litigation, and compensation payments. Most importantly, the health and safety of health care workers would be improved.

SUMMARY OF THE INVENTION

It is therefore an object of this invention to provide devices that improve the safety of hypodermic needles and other sharp instruments with applications to health care, research, and industry.

In one preferred embodiment, the present invention provides a device comprising: a sharp; and a cap engaging and holding the sharp, the cap including a sheath into which the sharp extends and which surrounds the sharp, the sheath including an open base region which engages a hub region on the sharp to hold the sharp in the sheath and including a top region covering a top portion of the sharp, the base region and the top region of the receptacle defining an axial direction extending from the center of the base region to the center of the top region, the hub region of the sharp including a means for mounting the sharp on a mounting device, the sheath leaving uncovered the means for mounting the sharp on the mounting device; a lateral member extending from the receptacle in a direction which is perpendicular to the axial direction of the sharp; and a handle connected to the lateral member and extending in a direction opposite to the axial direction.

In another embodiment, the present invention provides a safety cap for a sharp comprising: a sheath for receiving a sharp and including means for engaging a hub region of the sharp, the receptacle extending in an axial direction from a base region of the receptacle to a top region of the receptacle; a lateral member extending from the receptacle in a direction which is perpendicular to the axial direction of the sheath; a handle connected to the lateral member and extending in a direction opposite to the axial direction; and a hub capping slider including an opening through which the handle extends and which allows the slider to slide on the handle, the hub capping means including a hub capping receptacle for engaging and covering a hub of a sharp when the sharp is held in the cap receptacle and the slider is moved on the handle to a position adjacent to the hub of the sharp held in the cap receptacle.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Definitions

Figure 1:
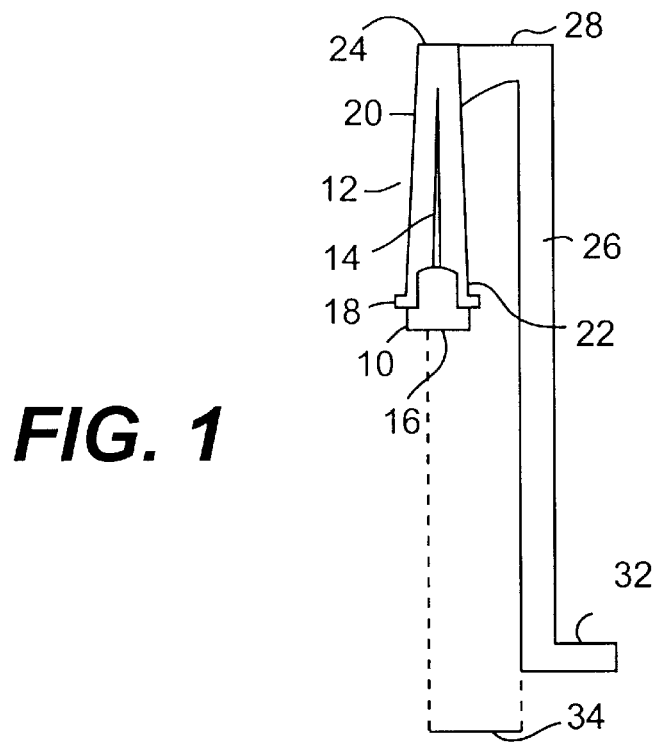
FIG. 1 illustrates one embodiment of a capped needle of the present invention.

For the purposes of the present invention the term "sharp" refers to device such as a needle, solid or hollow, or blade capable of piercing or cutting the skin. Examples of sharps include hypodermic needles, scalpels, bits, corers, injectors, aspirators, drills, blades, punches, etc.

For the purposes of the present invention, the term "axial direction" refers to the direction from the center of the base region of a sheath of a cap to the center of the top region of the sheath of the cap. Because the cap sheaths of the present invention are open at their bases, the center of the base region is a point in space at the base of a receptacle. The sheath of a cap for a sharp is designed to hold the sharp and prevent the sharp from coming in contact with a user.

For the purposes of the present invention, the term "target area" for a sharp refers to the area in the vicinity of the point of a needle or the cutting edge of a blade.

Description

Hypodermic needles and other sharp devices have been used for many years in industry, research, and medical practice. Hypodermic needles in particular, which consist of a hollow metal tube sharpened on one end in order to penetrate the skin or other substance, are attached to a syringe which is used to aspirate or inject volumes of fluid through the hollow barrel of the needle. In medical practice, hypodermic needles are most often used to inject medications into skin, subcutaneous tissues, muscle, blood vessels, or other tissues. Hypodermic needles are also used to aspirate fluid from body cavities and to transfer medications, samples, or reagents from stoppered bottles or other containers to other containers or devices.

Before use the hypodermic needle is sharp, but sterile. However, after use, the needle becomes contaminated with blood, body fluids, or residual fluid remaining from aspiration of samples from bottles. These contaminated hypodermic needles remain very sharp and easily penetrate the skin, directly depositing infectious agents into the body tissues of the medical worker. These injuries have a high incidence of transmission of hepatitis B and hepatitis C, as well as other infectious agents. Needle sticks from hypodermic needles occur in several ways: 1) accidental sticks that occur from improperly discarded uncapped needles, 2) accidental sticks that occur from the act of improperly discarding needles, 3) sticks that occur from attempts to recap the contaminated needle, 4) sticks that occur to the operator from an uncapped needle not in immediate use, but still on the equipment tray or in the operating field, 5) sticks that occur in the operating field from a misdirected needle, or 6) intentional sticks.

The present invention can decrease needle sticks occurring principally from improperly discarded uncapped needles, recapping injuries, improper disposal of needles, and sticks that occur to the operator from an uncapped needle not in immediate use, but still on the equipment tray or in the operating field by removing the hand from the vicinity of the contaminated needle and by ensuring that the needle is recapped prior to disposal or when not in use.

In one embodiment, the present invention provides a modified cap or sheath, preferably made of plastic, for a hypodermic needle that provides fundamental protection from needle sticks. This cap can be packaged with the needle or other sharp device.

Figure 2:
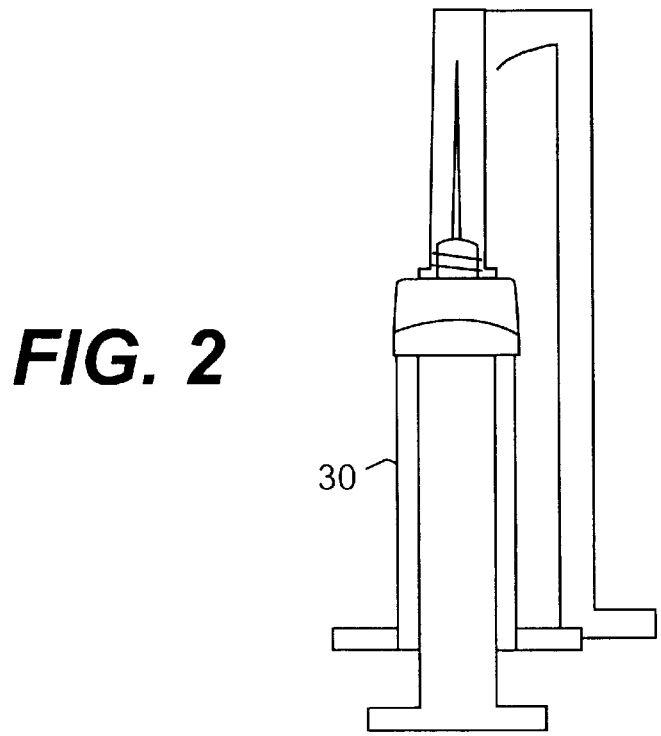
FIG. 2 illustrates the capped needle of FIG. 1 mounted on a syringe.
Figure 3:
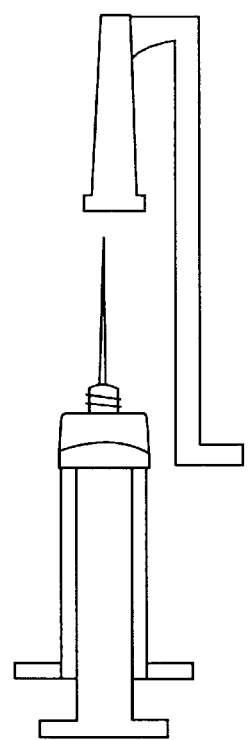
FIG. 3 illustrates a cap of the capped needle mounted on the syringe of FIG. 2 being removed from the needle.

FIG. 1 illustrates one embodiment of the present invention. As shown in FIG. 1, a hypodermic needle 10 is held in a cap 12. The needle 10 is a conventional hypodermic needle and includes a barrel 14 and a hub 16 having a circumferential lip 18 at the base of the hub 16. The cap includes a sheath 20 (shown in cross-section) into which the needle 10 extends in an axial direction. Sheath 20 includes a base region 22 and a top region 24 which define an axial direction extending from the base region 22 to the top region 24. A descending handle 26 is attached to the sheath 20 by a lateral member 28 which places the handle 26 away from the sheath 20 and is connected to the sheath 20 at a top side portion of the sheath 20. This arrangement of the sheath 20, handle 26 and lateral member 28 allows larger diameter devices to engage the needle 10 while the needle 10 remains safely within the sheath 20 as shown in FIG. 2. The handle 26 provides sufficient leverage to pull the needle 10 down on a mounting region (not shown) of a conventional syringe 30 With respect to a user, the handle 26 extends proximally from the sheath 20, thereby moving a user's fingers grasping the handle away from the needle 10. In the embodiment shown in FIGS. 1 and 2, the handle 26 includes a stop or gripping portion 32 which protrudes laterally so that the gripping portion 32 does not impede the seating of the needle 10 on larger diameter devices. Preferably a distance 34 between the center of the needle 10 and the inner edge of handle 26 is equal to the radius of the device on which the needle 10 is to be mounted. Once the needle 10 has been seated on syringe 30, the cap 12 can be removed from needle 10 as shown in FIG. 3.

In order to remove a used or contaminated needle 10, the cap 12 can be replaced on the needle and the handle 26 pulled down so that the hub 16 of the needle 10 will frictionally engage the sheath 20. This is essentially the reverse of the procedure shown in FIGS. 2 and 3. The syringe 30 can then be held upside down and the handle rotated around the syringe 30 until the needle 10 is loosened from engaging the syringe 30 and can be safely removed. This procedure resembles the procedure illustrated in FIGS. 1 and 2 except in reverse and upside down. Because of the design of the handle 26 of the present invention, a user's fingers are kept safely away from the contaminated needle 10 during the re-capping procedure. The used needle 10 and cap 12 can then be disposed of safely in a biohazard container 36 as shown in FIG. 4.

Figure 4:
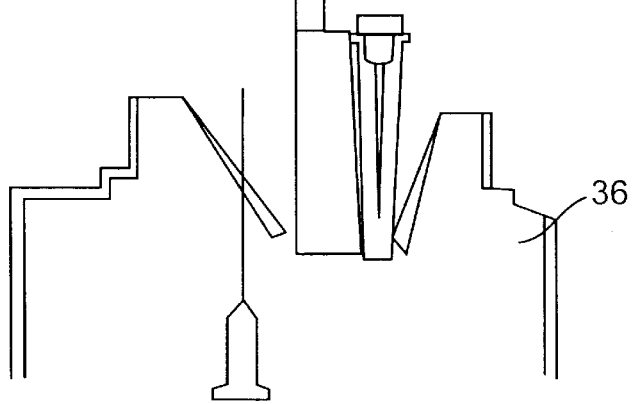
FIG. 4 illustrates a capped contaminated needle of the present invention being disposed of in a biohazard container.

As seen in FIG. 4, an important benefit of the present invention is the prevention of needle sticks associated with disposal of spent needles in biohazard containers. Needle sticks can occur from disposal of needles in biohazard sharps (spent needle) containers that are typical in any medical clinic or hospital. A problem with disposal of needles is the tendency of the needle to resist entrance into the container or the tendency of the needle to "jump out" again at the operator, resulting in a needle stick. The present safety cap minimizes this risk by allow the spent needle and cap to be placed into the biohazard container with the digits at a safe distance as shown in FIG. 4.

As seen in the embodiment of FIGS. 1 through 4, the cap 12 of the present invention includes a handle 26 that extends laterally and proximally (with respect to a user) to remove the user's hand from the needle 10 to be mounted on a syringe 30. The handle 30, which can be short or long, permits the cap 12 to be grasped without putting a user's fingers or hand within the target area (needle point or needle side) of contaminated hypodermic needle or other sharp device. Although simple in concept, the present invention is very effective in protecting a user from needle stick. Although the embodiment shown in FIGS. 1 through 4 only illustrates the use of the cap of the present invention with hypodermic needles on syringes, the cap of the present invention can also be used with other kinds of sharps mounted on other kinds of instruments, such as a scalpel blade on a long cylindrical scalpel.

The present invention has the following advantages: 1) it removes the operator's digits and hands from the target area (both from the immediate target area and from the plane of the target area) of the contaminated needle or other sharp device by extending first laterally and then proximally (with respect to a user); 2) the lateral extension of the handle increases the applications of this device by permitting physical accommodation of all sizes of syringes and medical devices (unlike other caps with handles) and removes the fingers laterally from the target area; 3) the proximal portion of the handle moves the fingers behind both the point and side of the contaminated needle or sharp device completely removing the fingers from the target area; 4) the handle is rigid and fused with the sheath permitting an excellent platform for attaching and removing needles and other sharp devices, even with Luer-Lok devices, because of this mechanical rigidity; 5) an optional gripping portion (rest or stop) can extend laterally from the handle, further removing the fingers from the contaminated needle or syringe and permitting larger devices to be accommodated than a handle protruding the opposite direction; 6) once the needle or other sharp device is seated, the cap can remain on further promoting the safety of this device, and duplicating the traditional uses of conventional caps, but with greater safety, 7) it facilitates recapping of the needle or other sharp device by following and promoting the OSHA guidelines regarding recapping; 8) it makes the cap larger and less likely to roll and be lost in an operating field; 9) facilitates the safe disposal of needles and will decrease injuries associated with placing needles in biohazard receptacles due to the lack of physical proximity of the fingers with the disposal device.

Although the cap of the present invention is only shown in FIGS. 1 through 4 as being used for syringes having disposable needles, the cap of the present invention can also be used with syringes having permanent needles. In this case, the cap of the present invention would be used to cap the needle on the syringe and the entire capped syringe would then be disposed of in a biohazard or other suitable container.

A number of other embodiments of the present invention are shown in FIGS. 5, 6, 7, 8 and 9. In the embodiment shown in FIG. 5, a cap 38 has a lateral member 40 is in the shape of a flat four-sided flange which is joined along the entire length of a sheath 42 (shown in cross-section). A handle 44 extends proximally from the lateral member 40. The handle 44 includes a gripping portion 46.

Figure 6:
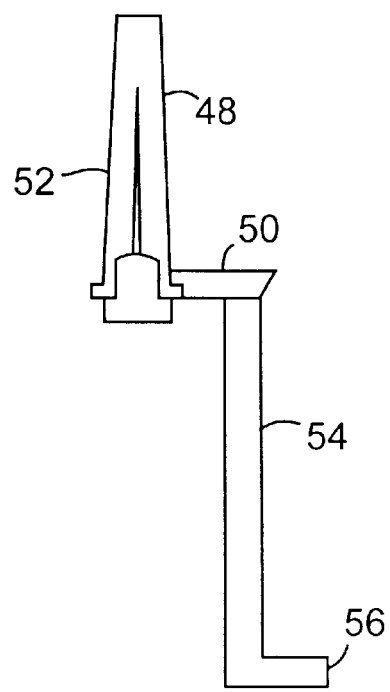
FIG. 6 illustrates a third embodiment of a capped needle of the present invention.

In the embodiment shown in FIG. 6, a cap 48 includes a lateral member 50 that extends from the base of a sheath 52 (shown in cross-section). A handle 54 extends proximally from the lateral member 50. The handle 54 includes a gripping portion 56.

Figure 7:
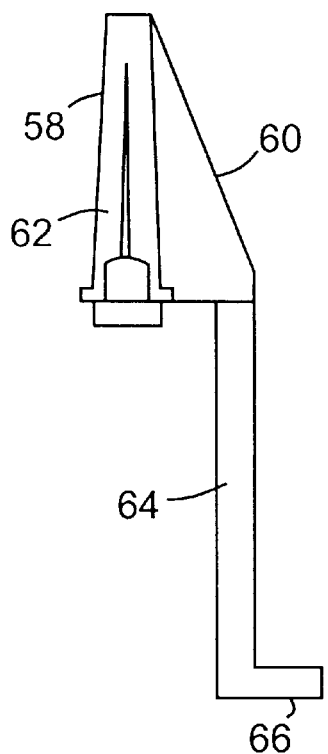
FIG. 7 illustrates a fourth embodiment of a capped needle of the present invention.

In the embodiment shown in FIG. 7, a cap 58 has a lateral member 60 in the shape of a triangular flat flange that is joined along the entire length of a sheath 62 (shown in cross-section). A handle 64 extends proximally from the lateral member 60. The handle 64 includes a gripping portion 66.

Figure 8:
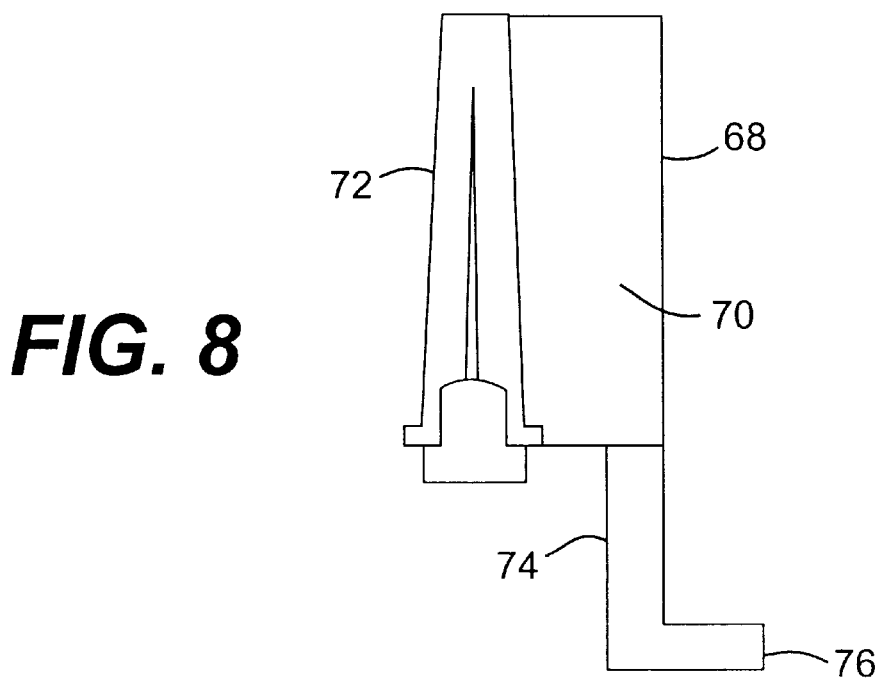
FIG. 8 illustrates a fifth embodiment of a capped needle of the present invention.

In the embodiment shown in FIG. 8, a cap 68 has a lateral member 70 is in the shape of a flat four-sided flange which is joined along the entire length of a sheath 72 (shown in cross-section). A handle 74 extends proximally from the lateral member 70. The handle 74 includes a gripping portion 76. The embodiment of FIG. 8 closely resembles the embodiment of FIG. 5, except the handle 74 is considerably shorter.

Figure 9:
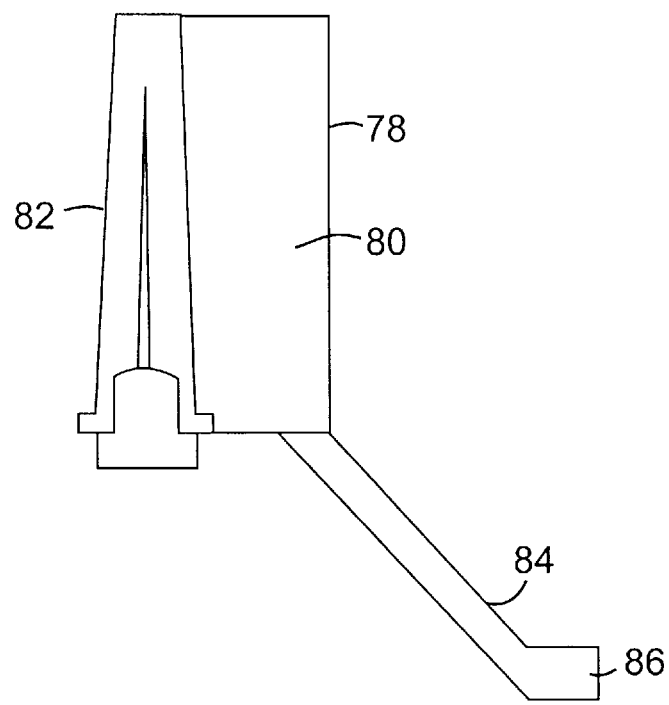
FIG. 9 illustrates a sixth embodiment of a capped needle of the present invention.

In the embodiment shown in FIG. 9, a cap 78 has a lateral member 80 is in the shape of a flat four-sided flange which is joined along the entire length of a sheath 82 (shown in cross-section). A handle 84 extends proximally and diagonally from the lateral member 80. The handle 84 includes a gripping portion 86. The embodiment of FIG. 9 closely resembles the embodiment of FIG. 5, except the handle 84 extends at an angle instead of straight from the lateral member 80.

As evidenced by the embodiments shown in FIGS. 5 through 8, multiple variations of the cap of the present invention are possible which include a handle which is laterally spaced from the sheath of the cap and extends proximally from the sheath of the cap. The handle of the invention, which protrudes laterally and proximally (with respect to a user), facilitates recapping of a needle, even when OSHA guidelines are followed because the cap can be carefully directed. If, during a recapping attempt, the needle misses the cap orifice, and the needle moves to the side of the cap, the digits and hands are safely out of the target field of the needle. Thus, the risk of injuries from sharps and transmission of infectious agents are greatly reduced and the safe recapping of the needle is achieved. Removal or recapping of needle is routinely required in medical procedures when substances are aspirated from vials with one sized needle and injected with another. Recapping of the needle using the present invention can also decrease the incidence of injury from stray uncapped needles.

Figure 10:
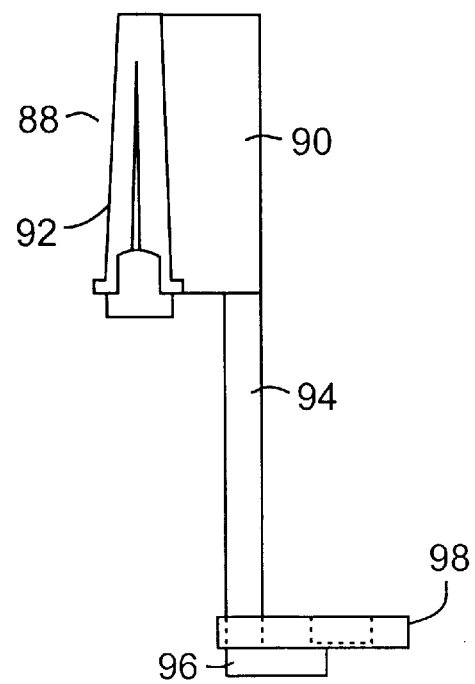
FIG. 10 illustrates a seventh embodiment of a capped needle of the present invention with a sliding needle lock in a position that allows the cap of the present invention to be lowered on a syringe.
Figure 11:
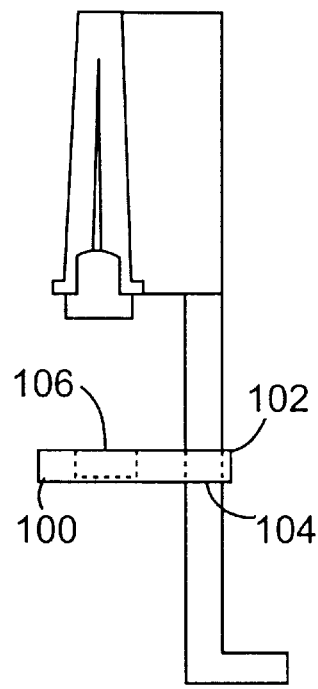
FIG. 11 illustrates the capped needle of FIG. 10 with the sliding needle lock in an intermediate position.
Figure 12:
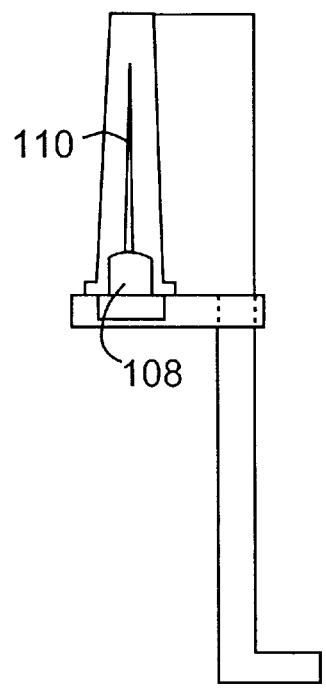
FIG. 12 illustrates the capped need of FIG. 11 with the sliding needle lock capping the hub of a disposable needle.

Although the embodiments described above provide safer uncapping and recapping of hypodermic needles, they do not prevent the needle from coming loose from the cap. This is important because a loose contaminated needle can cause further inadvertent injury, particularly if the needle is improperly disposed of where it could accidentally injury or infect other workers. FIGS. 10, 11 and 12 show an embodiment of the present invention which addresses this problem.

Figure 5:
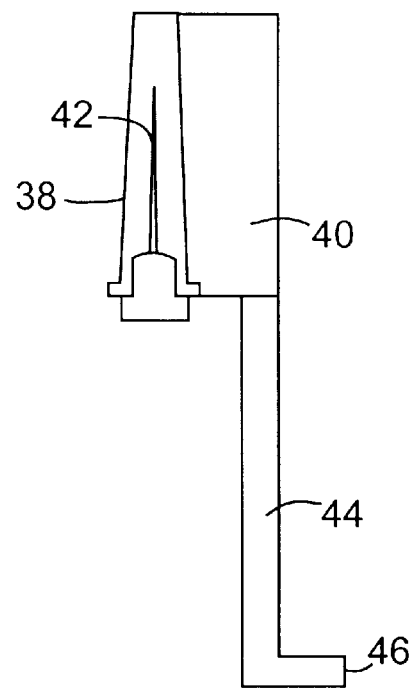
FIG. 5 illustrates a second embodiment of a capped needle of the present invention.

In the embodiment shown in FIG. 10, a cap 88, which resembles the cap 38 of FIG. 5, has a lateral member 90 is in the shape of a flat four-sided flange which is joined along the entire length of a sheath 92 (shown in cross-section). A handle 94 extends proximally from the lateral member 90. The handle 94 includes a gripping portion 96. A sliding needle lock 98 slides up and down on the handle 94 as shown in FIGS. 10 and 11. The sliding needle lock 98 has a circular portion 100 attached to an oblong portion 102 which has an opening 104 (shown by shadow lines) which allows the sliding needle lock to slide on handle 94. The circular portion 100 includes an interior hub capping recess 106 (shown by shadow lines) which engages a hub 108 of a needle 110 when the sliding needle lock 98 is slid up beneath the needle 110 as shown in FIG. 12. As shown in FIG. 10, 11, and 12, the sliding needle lock 98 is able to rotate at least 180 degrees on the handle 94, so that the sliding needle lock 98 can be rotated out of the way when the cap 88 is used to place a needle on a syringe (not shown), while allowing the sliding needle lock 98 to be rotated to cap the hub 108 of the needle 106 when the contaminated needle 110 is to be removed form the syringe. The gripping portion 96 of the handle 94 acts as a stop, so that the sliding needle lock 98 remains integrated with the cap 88 and does not detach and cannot be lost.

The embodiment shown in FIGS. 10, 11 and 12 has all the previous mentioned advantages of the prior described embodiments, as well as further advantages including: 1) integration with the cap which prevents loss and separation of the components, 2) the ease of advancing the locking mechanism with the needle already safely ensconced in the needle cap, 3) further protection of the operator's fingers, and 4) protection for other workers if the recapped and locked needle is inadvertently improperly disposed of.

Figure 13:
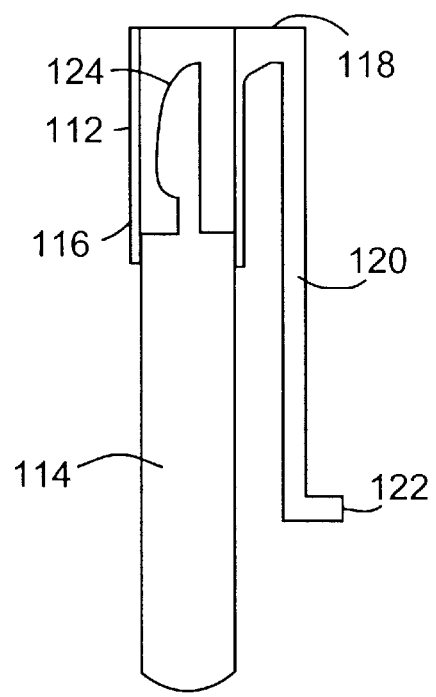
FIG. 13 illustrates an embodiment of a capped scalpel of the present invention.
Figure 14:
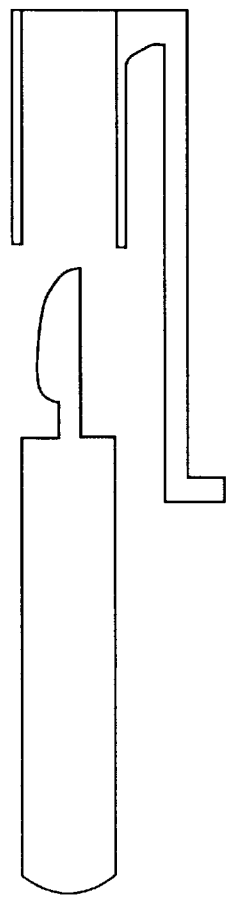
FIG. 14 illustrates the capped scalpel of FIG. 13 with the cap removed.

Although the present invention has been primarily described with respect to capping and disposing of hypodermic needles, the safety caps of the present invention can be used in similar ways with other with other sharp medical instruments. For example, FIGS. 13 and 14 illustrate the use of a safety cap 112 with a scalpel 114. The safety cap 112 includes a tubular sheath 116, a lateral member 118 and a proximally extending handle 120 attached to the sheath 116 by the lateral member 118. Handle 120 also includes a gripping portion 122. Prior to use, the scalpel 114 can be capped as shown in FIG. 13 and then uncapped for use as shown in FIG. 14. Once the scalpel 114, the safety cap 112 can be placed again on the scalpel 114 the handle 120, as shown in FIG. 13. The capped contaminated scalpel 114 can then be disposed of in a biohazard container or similar receptacle.

Although in the embodiment shown, the scalpel 114 has an integral blade 124, in some circumstances, the blade of a scalpel can be disposable. In the case of disposable scalpel blade, the cap of the present invention can be used to place the blade on a scalpel and remove a contaminated blade from a scalpel in a fashion similar to that shown above for disposable hypodermic needles placed on and removed from syringes. Also, if the scalpel blade is disposable, the cap of the present invention can include a sliding lock similar to the sliding needle lock shown in FIGS. 10, 11, and 12, which caps the base of the disposable scalpel blade. As fully conventional to those skilled in the art, the danger from hypodermic needles and other sharp instruments has been reduced by the design of a safety cap which reduces the chance of an accidental stick or penetration of the skin. The safety cap utilizes fundamental changes in cap design that result in substantial protection of the operator's hands from penetration by the sharp surfaces of contaminated medical instruments.

The present invention has wide applicability for capping sharp instruments used in medical science and industry, and particularly to hypodermic needles that result in the bulk of sharp instrument injuries to medical workers. The caps of the present invention provide caps provide greater safety greater than that of standard caps, prevent of needle sticks with recapping, offer greater user satisfaction, and provide greater safety in disposal of these instruments.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed:

1. A device comprising:
   a sharp; and
   a cap engaging and holding said sharp, said cap including
      a sheath into which said sharp extends and which surrounds said sharp, said sheath including an open base region which engages a hub region on said sharp to hold said sharp in said sheath and including a top region covering a top portion of said sharp, said base region and said top region of said sheath defining an axial direction extending from the center of said base region to the center of said top region, said hub region of said sharp including a means for mounting said sharp on a mounting device, said sheath leaving uncovered said means for mounting said sharp on the mounting device;
      a lateral member extending from said sheath in a direction that is perpendicular to the axial direction of said sharp, said lateral member comprising a flange having one edge connected to said sheath along substantially the entire length of said sheath; and
      a handle connected to said lateral member and extending in a direction opposite to said axial direction.

2. The device of claim 1, wherein said handle extends in a direction substantially parallel to the axial direction of said sheath.

3. The device of claim 1, wherein said handle extends at angle away from said axial direction of said sheath.

4. The device of claim 1, wherein said lateral member comprises a quadrilateral flange.

5. The device of claim 1, wherein said lateral member comprises a triangular flange.

6. The device of claim 1, wherein said sharp comprises a hypodermic needle.

7. The device of claim 6, further comprising a syringe on which said hypodermic needle is removeably mounted.

8. The device of claim 6, further comprising a syringe on which said hypodermic needle is mounted.

9. The device of claim 1, wherein said sharp comprises a blade.

10. The device of claim 1, wherein said sharp comprises a scalpel comprising a blade and scalpel handle.

11. The device of claim 1, further comprising:
    a hub capping slider including an opening through which said handle extends and which allows said slider to slide on said handle, said hub capping slider including a hub capping receptacle for engaging and covering a hub of a sharp when the sharp is held in said hub capping receptacle and said slider is moved on said handle to a position adjacent to the hub of the sharp held in said hub capping receptacle.

12. A safety cap for a sharp comprising:
    a sheath for receiving a sharp and including means for engaging a hub region of said sharp, said sheath extending in an axial direction from a base region of said sheath to a top region of said sheath;
    a lateral member extending from said sheath in a direction which is perpendicular the axial direction of said sheath;
    a handle connected to said lateral member and extending in a direction opposite to said axial direction; and
    a hub capping slider including an opening through which said handle extends and which allows said slider to slide on said handle, said hub capping slider including a hub capping receptacle for engaging and covering a hub of a sharp when the sharp is held in said hub capping receptacle and said slider is moved on said handle to a position adjacent to the hub of the sharp held in said hub capping receptacle, said hub capping slider being rotatably mounted on said handle so that when said hub capping receptacle may be rotated to capping position directly beneath said sheath and a non-capping position 180° away from said capping position.

13. The safety cap of claim 12, wherein a proximal end of said handle includes a means for preventing said hub capping slider from sliding off said handle.

* * * * *